United States Patent [19]

Webster et al.

[11] 4,306,089
[45] * Dec. 15, 1981

[54] PROCESS FOR THE PRODUCTION OF FORMALDEHYDE

[75] Inventors: Dennis E. Webster; Ian M. Rouse, both of Royston, England

[73] Assignee: Johnson, Matthey & Co., Limited, London, England

[*] Notice: The portion of the term of this patent subsequent to Jun. 17, 1997, has been disclaimed.

[21] Appl. No.: 55,402

[22] Filed: Jul. 6, 1979

Related U.S. Application Data

[63] Continuation-in-part of Ser. No. 895,812, Apr. 12, 1978, Pat. No. 4,208,353.

[30] Foreign Application Priority Data

Apr. 15, 1977 [GB] United Kingdom ............... 15761/77

[51] Int. Cl.$^3$ .............................................. C07C 45/16
[52] U.S. Cl. ................................... 568/472; 568/473; 568/474
[58] Field of Search ....................... 568/472, 473, 474

[56] References Cited

U.S. PATENT DOCUMENTS

| | | | |
|---|---|---|---|
| 2,307,934 | 1/1943 | Coder et al. | 568/472 |
| 3,174,911 | 3/1965 | Webb et al. | 568/473 |
| 3,965,195 | 6/1976 | Buschmann et al. | 568/472 |
| 4,208,353 | 6/1980 | Weber et al. | 568/472 |

*Primary Examiner*—Natalie Trousof
*Assistant Examiner*—James H. Reamer
*Attorney, Agent, or Firm*—Cushman, Darby & Cushman

[57] ABSTRACT

This invention relates to the production of formaldehyde and to catalysts which may be used therefore. In more detail the invention relates to a process for the production of formaldehyde from methanol includes the passage, at an elevated temperature, of a gas stream containing methanol and oxygen through a catalyst, the catalyst comprising a monolithic support provided with channels for passage therethrough of the gas stream and with the channel wall surfaces coated or impregnated with one or more elements selected from the group consisting of copper, silver, gold and iron.

6 Claims, No Drawings

PROCESS FOR THE PRODUCTION OF FORMALDEHYDE

This application is a continuation-in-part of Ser. No. 895,812, filed Apr. 12, 1978, now U.S. Pat. No. 4,208,353.

This invention relates to the production of formaldehyde and to catalysts which may be used therefore.

It is known that formaldehyde may be manufactured by a combined oxidation and dehydrogenation using an air or oxygen plus methanol feedstock:

The catalyst most frequently used is pure silver in crystalline, i.e. granular, form in a catalyst bed. U.S. Pat. Nos. 3,174,911 and 3,965,195 each disclose a process for the manufacture of formaldehyde from methanol. These prior patents disclose the use of dehydrogenation catalysts in particulate form (e.g. in the form of granules, pellets rings and spheres) and the actual catalyst materials disclosed include silver, copper, iron and gold. The use of such particulate catalysts reduces the "throughput" or "space velocity" of reactants passing through a catalyst bed and it is an object of the present invention to improve the "throughput" and also the yield in the conversion of methanol to formaldehyde.

According to one aspect of the present invention, a process for the production of formaldehyde from methanol includes the passage, at an elevated temperature, of a gas stream containing methanol and oxygen through a catalyst comprising a monolithic support provided with channels for passage therethrough of the gas stream and with the channel wall surfaces coated or impregnated with one or more elements selected from the group copper, silver, gold and iron.

According to a second aspect of the present invention there is provided, in a process for the production of formaldehyde from methanol which comprises passing at an elevated temperature sufficient to convert the methanol to formaldehyde by oxidative dehydrogenation, the modification which comprises using, as the catalyst, one comprising a monolithic support provided with channels for passage therethrough of the gas stream the channel wall surfaces being coated or impregnated with one or more elements selected from the group consisting of copper, silver, gold, and iron.

Preferably the elements copper, silver, gold and iron are in metallic form but they may be in chemically combined form. Alternatively the iron may be present in combined form as iron molybdate.

The invention also includes a catalyst comprising a monolithic support provided with channels for passage therethrough of reactants and with the channel wall surfaces coated or impregnated with one or more elements selected from the group copper, silver, gold and iron.

By "elevated temperature" we mean a temperature such that when the gas stream is in contact with the catalyst a significant proportion of the methanol is converted to formaldehyde by the oxidative dehydrogenation reaction referred to above. The temperature is preferably within the range 500° C.–700° C.

The gas stream is preferably at a pressure within the range 0.5 to 2.0 atmospheres and has a space velocity through the catalyst within the range 5000 to 10,000 hr.$^{-1}$. The gas stream passing through the catalyst normally also contains steam and recycled methanol.

The monolithic support may be either metallic or ceramic. Ceramic supports are preferably of the "honeycomb" type having a regular array of gas flow channels. Suitable materials which may be used to constitute the ceramic support are zircon-mullite, mullite, alpha alumina, sillimonite, magnesium silicates, kaolin clays, zircon, petalite, spodumene, cordierite and most alumino-silicates.

Proprietary products suitable for the monolithic support are described in U.S. Pat. No. 3,397,154 (Talsma), U.S. Pat. No. 3,498,927 (Stiles) and British Pat. No. 882,484 (Corning). Examples are "Torvex" (Registered Trade Mark) which in one convenient form is a mullite honeycomb having eight corrugations per inch and an alumina washcoat; "Thermacomb" (Registered Trade Mark), a cordierite honeycomb supplied by the Minnesota Mining and Manufacturing Corporation and M20 a cordierite honeycomb supplied by Corning Glass.

Preferably the ceramic honeycomb structure has deposited thereon a first coating of a refractory metal oxide which is then further impregnated or coated with one or more of the catalytic metals specified above. Suitable refractory metal oxides comprising the said first coating are one or more of the oxides of B, Al, Si, Be, Mg, Ca, Sr, Ba, Sc, Y, Ti, Zr, Hf, Th, the lanthanides and the actinides. Preferred refractory metal oxide layers comprise members of the gamma or activated alumina family. This can be prepared, for example, by precipitating a hydrous alumina gel and, thereafter, drying and calcining to expel hydrated water and provide active gamma alumina. We prefer to use British Aluminium Co. FRF 80 alumina tri-hydrate and convert it to activated alumina by drying and firing as described above.

A metallic monolith support is preferred to a ceramic support. As supports, metallic monoliths give a lower pressure drop and possess 1½–3 times the surface to volume ratio obtained with a ceramic honeycomb substrate. The normal ceramic substrate surface area is 600-700 sq. ft. per cubic foot of substrate. Examples are proprietary products M20 (Corning) which has a surface area of 576 sq. ft/ft$^3$ and Grace 400 cell which is 780 sq.ft/ft$^3$. This is the highest obtained so far and should be compared with 1100 sq. ft/ft$^3$ for 0.003" thick metal and 2000 sq. ft/ft$^3$ for 0.002" thick metal sheet.

We prefer to use foil of thickness between 0.0015 and 0.0045 inch and more preferably of thickness 0.002 inch corrugated and assembled to form a structure having approximately 400 cells per square inch when considered in cross-section. A preferred range of cell sizes is 200–800 cells per square inch. Suitable surface to volume ratios are 1200 sq. ft. per cubic foot with 400 cells per square inch and 2000 sq. ft. per cubic foot with 800 cells per square inch.

In one embodiment of the invention the catalytic metals Cu, Au, Ag and Fe as defined herein may be fabricated in the form of metallic foil monolithc direct. For example a Cu-Ag foil momolith can be used. Other metals which may be used for fabrication of the monolith support are those capable of withstanding high temperature and rigorous oxidising conditions. Examples of such base metal alloys are nickel and chromium alloys having an aggregate Ni+Cr content greater than 20% by weight and alloys of iron including at least one of the elements chromium (3-40 wt %), aluminium (1-10 wt %), cobalt (trace—5 wt %), nickel (trace—72 weight %) and carbon (trace—0.5 weight %). Quantities of trace elements which may usefully be present in such alloys to improve strength and oxidation—and heat-resistance are:

|    | %    | w/w  |
|----|------|------|
| Si | 0.2  | 0.9  |
| Mn | 0.2  | 0.7  |
| Zr | 0.01 | 0.20 |
| Cu | 0.01 | 0.15 |
| Nb | 0.01 | 0.3  |
| Ta | 0.8  | 1.2  |
| Ti | 0.8  | 1.2  |
| Co | 0.01 | 1.0  |
| Ca | 0.01 | 0.5  |
| C  | 0.01 | 0.1  |

One range of heat resistant alloys which may comprise the extended metal substrate are preferably those alloys having a minimum nickel plus chromium content of 20% by weight. Typical alloys which therefore may be used for the extended metal substrate are high nickel and chromium stainless steels and proprietary products such as "INCONEL" (Registered Trade Mark) 600 and "INCONEL" 601.

Other examples of base metal alloys capable of withstanding the rigorous conditions required are the iron-aluminium-chromium alloys which also contain yttrium. These contain 0.5-12 wt % Al, 0.1-3.0 wt % Y, 0-20 wt % Cr and balance Fe. These are described in U.S. Pat. No. 3,298,926. Another range of Fe-Cu-Al-Y-alloys contain 0.5-4 wt % Al, 0.5-3.0 wt % Y, 20.0-95.0 wt % Cr and balance Fe. These are described in U.S. Pat. No. 3,027,252.

An example of metallic substrate made in accordance with this invention comprises a roll of corrugated sheet of a heat resistant alloy, or of the catalytic metal, interleaved with a non-corrugated sheet of such an alloy or metal. Alternatively two corrugated sheets may be used with the corrugations in each sheet parallel with each other or at an angle to each other. Other ways of producing channels in the substrate including crimping, folding, indenting and perforating one or both of the sheets. The surface area of substrates made in thin metals by these techniques is normally much greater than that obtained with ceramic honeycombs or with particulate catalyst supports of the same overall volume. A coiled substrate may then be provided with a firmly adherent oxide coating which is porous and adsorbent and has a high surface area and which acts as the carrier for the second catalytically active layer containing one or more of the catalytic metals as herein defined.

We prefer to provide the metallic substrate with a first firmly adherent oxide layer in an essentially two stage process. In a first stage the metallic substrate is oxidised to provide a thin first oxide layer which acts as a key. A preferred method is to carry out thermal oxidation by maintaining the formed metallic substrate at from 1000°-1200° C. in air or moist cracked ammonia vapour for 1 hour. The higher temperature is required with very oxidation resistant alloys such as the Kanthal range and the moist hydrogen atmosphere is preferred with alloys having a high Ni content.

In a second stage the adherent oxygen containing or oxide film may be produced by any one of several known methods including chemical techniques. The film must be of sufficient thickness to provide adequate absorbtive capacity for retaining the catalytically active alloy comprising one or more of the platinum group metals. The film is preferably from 0.0004 to 0.001 inch thick.

Where aluminium is present in the alloy forming the extended metal substrate the first stage oxide film may be produced by treating the aluminium containing surface with a solution of an alkaline carbonate usually a sodium carbonate chromate solution. The film may be produced by the anodic oxidation of the metal surface whereby the metal is made the anode in an electrolytic solution. In anodising aluminium containing surfaces, a 15% sulphuric acid solution is commonly employed as the electrolyte but other acid electrolytes such as chromic acid, oxalic acid, phosphoric acid and sometimes boric acid may be used. The oxide film to which this invention relates is deliberately positioned and does not include the relatively thin natural oxide films which sometimes occur on metal surfaces which have been exposed to the atmosphere.

One method of forming a first stage alumina layer on these alloys which do not contain sufficient aluminum to form their own alumina layer upon oxidation is the use of Calorising (Registered Trade Mark). This involves the vapour deposition of an aluminium coating followed by anodising or heating in an oxygen-containing gas. Alternative coatings such as chromate, phosphate, silica or silicate, or zirconia may all be deposited by known methods.

There are many different techniques for the preparation of the second stage high surface area catalytically active refractory metal oxide wash coat containing one or more of the refractory metal oxides which confer beneficial properties as regard ageing and inertness to deposited catalytic metals at high temperature under oxidising and reducing conditions. Some of these are described below:

A preferred adherent oxide coating deposited upon the extended metal substrte is alumina.

One method for the deposition of hydrous alumina is proposed in U.S. Pat. No. 2,406,420. Any convenient aluminium compound such as alkali metal aluminates and aluminum salts may be used as the starting material. Either acidic or basic precipitants are used, depending upon the character of the starting material. Suitable acidic precipitants are ammonium chloride, ammonium sulphate, ammonium nitrate, hydrochloric acid, nitric acid, etc. Suitable basic precipitants are ammonium hydroxide, sodium hydroxide, hexa-methylene, tetramine, etc.

Another method is to precipitate the hydrous alumina from an alkali metal hydroxide directly on to the extended metal substrates forming part of the present invention. If the aluminate solution is maintained at a temperature of 60°-85° C. a film or coating of alpha alumina trihydrate (Gibbsite) is deposited. Subsequent heating at from 25°-180° C. converts the monohydrate to gamma alumina without loss of the very high surface area coating which is produced by this method. The high surface area results from the formation of hexagonal crystal aggregates of approximate size 8×8×20 microns. Micropores of size 40Å diameter are present in the hexagonal crystal aggregates but appear to play no part in the catalytic activity of the structure.

We prefer a washcoat loading which is within the range of 5-30% by weight of the metallic monolith substrate. A suitable loading of $Al_2O_3$ on Kanthal D having 400 cells per square inch is 10% by weight. The surface area of the aluminium is 50–500 square meters per gram of alumina. The aluminate method of deposition of alumina, described above, gives a surface area of from 120–160 square meters per gram of alumina.

An alternative preferred method for the deposition of an adherent washcoat on the metallic substrate is to prepare a slurry of a pre-activated Gibbsite (alumina trihydrate) and an alumina monohydrate having a solid liquid ratio of between 25 and 50% and a pH less than 7 and using this to impregnate the shaped substrate by complete immersion. The exact strength of the slurry used (which may be determined by trial and error) should be sufficient to produce an alumina washcoat of the required thickness. The substrate is then allowed to dry in warm air and finally fired for 2 hours at 450° C. to form chi and gamma alumina in adherent coating up to 0.002 in. thick on the metallic substrate. Crystal aggregates of diameter 3–7 microns are produced having micropores of approximately the same size, i.e. 40 Å in diameter.

A further alternative method of deposition of an adherent alumina washcoat on the metallic substrate is to use a slurry of alpha alumina monohydrate. After firing at 450° C. gamma alumina is formed having a surface area generally between 180 and 300 square meters per gram. Gamma alumina is added to alpha alumina monohydrate at the slurrying stage before firing in order to form a thixotropic mixture. Crystallite or crystal aggregates of 20–100 Å diameter are formed. Micropore diameters remain the same at 40 Å.

Suitable proprietary alumina trihydrates (Gibbsite) are "FRF 80" supplied by British Aluminium Chemicals Ltd. and "C 333" supplied by Reynolds. Suitable alumina monohydrates (Boehmite) are "Sol-Gel Alumina" supplied by the United Kingdom Atomic Energy Authority. "Dispal M" supplied by Conoco and "Condea F" also supplied by the Conoco Group. Gibbsite is added to "Sol-Gel Alumina" (which is micro-crystalline Boehmite) at the slurrying stage in order to form a thixotropic mixture.

Optionally one or more of the oxides titania, zirconia, hafnia, and thoria may be present in the alumina for the purpose of providing additional stabilisation of the intermediate oxide (washcoat) layer. Other rare earth oxides, alkaline earth oxides and alkali metal oxides may also be used.

Many of the aluminum-containing metallic substrates according to the present invention have the property of oxidising "inwards." That is to say we believe that a factor contributory to the success of the present invention is the fact that the extended metal substrate itself, which forms part of the catalytic structure of the present invention has a tendency to oxidise under very strongly oxidising conditions in such a way that the first layer of adherent oxide film does not tend to grow over or cover the outermost layer of the catalytic metal, iron, copper, silver or gold.

Impregnation or deposition of one or more of the catalytic metals, upon the first refractory metal oxide containing adherent layer may be accomplished by known methods of deposition of catalytically active metals on washcoats or other supports, e.g. if a high surface area refractory metal oxide is the adherent oxygen containing film, the support may be immersed in a solution of water soluble inorganic salt or salts of the metal. In the case of silver a suitable method used would be to immerse the oxide coated substrate in a bath containing hot ammoniacal silver nitrate. On removing the unit from the bath the excess solution is drained before allowing the monolith to dry. The impregnated silver species may then be reduced to metallic silver by immersing in a bath of boiling water containing approximately 10 grams/liter dextrose. The bath is maintained at approximately pH8 by the addition of sodium bicarbonate. The catalyst thus obtained is again drained and dried.

If the catalyst metal is iron, present as iron molybdate, this may be present in one of the forms $FeMoO_4$, $Fe_2(MoO_4)_3$, $Fe_2(MoO_4)_3 MoO_3$. Iron (as one of the forms of iron molydate) and silver are the preferred catalytic metals for deposition on the monolith.

The product gases pass through a water cooled condenser where a proportion of the formaldehyde, unreacted methanol and steam are condensed.

A subsequent absorber scrubs the remaining gases in a circulating formaldehyde (Formalin) solution. Formic acid produced may be removed by an ion exchange resin.

The invention includes formaldehyde and formalin when made by a process according to the present invention.

The invention will now be described with reference to the following examples of supported silver catalysts.

The silver may be deposited directly onto the support material, or supported onto an intermediate material which is itself applied to a further support having better thermal or mechanical properties.

The supports used were:

(A) A cordierite ceramic support (Corning Glass, Type M20) of the unitary type having a mulitiplicity of parallel channels of square section. 300 channels per square inch was the channel density measured across the face of the unit which was 2' diameter and 3' long.

(B) A similar unit was made from Fecralloy steel by winding together flat and crimped sheets of the metal around a central spindle. The thickness of the metal was 0.002', and the dimensions of the unit were 2' diameter by 3' long. The density of the channels in this unit was 400 per square inch of surface on the face of the unit. The quantity of silver applied to the units was such as to give a 1 percent W/W loading by the application of an ammoniacal solution of silver nitrate and the use of glucose as the reducing agent. In the case of the Fecralloy steel support the unit was oxidised at 1200° C. for 2 hours prior to the application of the silver. This enables a layer of aluminia to be formed at the surface of the metal.

In operation the catalyst unit was contained within an electrically heated portion of a stainless steel tubular reactor. Liquid methanol from a metering pump and air/nitrogen from a cylinder supply entered a heated mixing/vaporising zone at the top of the reactor. From here the gasses passed through the catalyst, and immediately entered a water cooled "quenching" chamber. Products and unreacted methanol were then collected in a receiving vessel and "scrubbing" system.

EXAMPLE 1

A catalyst based on Fecralloy steel and containing about 1% by weight of silver was used. The flow rate was 220 ml methanol per hour in a carrier gas consisting chiefly of air to give an overall content of air of 55 volume % at an overall pressure only slightly in excess of 1 atmosphere. The temperature of the inlet gas to the catalyst was set at 220 C. and the catalyst was aged for 5 hours under these conditions. The yield of formaldehyde in the outlet gas was found to be 85%, the remainder being essentially unreacted methanol.

EXAMPLE 2

A similar catalyst to that used in Example 1 but using a methanol flow rate of 120 ml per hour, and an inlet temperature of 300° C. The yield of formaldehyde in this case was 81%.

EXAMPLE 3

The system in Example 2 was modified by increasing the proportion of air to 60%, the other condition remaining the same. The conversion of the methanol in this case had risen to 99%.

EXAMPLE 4

A catalyst based on a ceramic monolith (Corning M20) having a silver content of 1% W/W was used. In this case the flow rate of methanol was 443 ml per hour in a gas stream containing 55% air. The temperature of the gas at the inlet to the catalyst was 300° C. In this system 71% of the methanold was converted to formaldehyde.

From the foregoing examples it will be appreciated that the process according to the invention results in a very high yield in the conversion of methanol to formaldehyde.

What we claim is:

1. A process for the production of formaldehyde from methanol includes the passage, at an elevated temperature, of a gas stream containing methanol and oxygen through a catalyst, the catalyst comprising a monolithic support provided with channels for passage therethrough of the gas stream and with the channel wall surfaces coated or impregnated with at least one member of the group consisting of copper, silver, gold and iron.

2. In a process for the production of formaldehyde from methanol which comprises passing at an elevated temperature sufficient to convert the methanol to formaldehyde by oxidative dehydrogenation the modification which comprises using, as the catalyst, one comprising a monolithic support provided with channels for passage therethrough of the gas stream the channel wall surfaces being coated or impregnated with at least one member of the group consisting of copper, silver, gold and iron.

3. A process according to claim 2 wherein the elements copper, silver, gold and iron are in metallic form.

4. A process according to claim 2 wherein, the elements copper, silver, gold and iron are in chemically combined form.

5. A process according to claim 2, in which iron is present as iron molybdate.

6. A process according to claim 1 wherein the gas stream contains steam and recycled methanol.

* * * * *